(12) United States Patent
Mainguet et al.

(10) Patent No.: US 10,949,638 B2
(45) Date of Patent: Mar. 16, 2021

(54) MANUFACTURING PROCESS OF A PIXEL ARRAY OF A THERMAL PATTERN SENSOR AND ASSOCIATED SENSOR

(71) Applicants: IDEMIA IDENTITY & SECURITY FRANCE, Courbevoie (FR); COMMISSARIAT A L'ENERGIE ATOMIQUE ET AUX ENERGIES ALTERNATIVES, Paris (FR)

(72) Inventors: Jean-Francois Mainguet, Grenoble (FR); Joel-Yann Fourre, Grenoble (FR); Christophe Serbutoviez, Grenoble (FR); Mohammed Benwadih, Grenoble (FR)

(73) Assignees: IDEMIA IDENTITY & SECURITY FRANCE, Courbevoie (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/542,236

(22) Filed: Aug. 15, 2019

(65) Prior Publication Data
US 2020/0057879 A1 Feb. 20, 2020

(30) Foreign Application Priority Data
Aug. 16, 2018 (FR) ...................................... 1857511

(51) Int. Cl.
*G06K 9/00* (2006.01)
*A61B 5/1172* (2016.01)
(Continued)

(52) U.S. Cl.
CPC .......... *G06K 9/0002* (2013.01); *A61B 5/1172* (2013.01); *G01J 5/34* (2013.01);
(Continued)

(58) Field of Classification Search
CPC ....... G06K 9/0002; G06K 9/209; H01L 37/02
See application file for complete search history.

(56) References Cited

U.S. PATENT DOCUMENTS 6,091,837 A 7/2000 Dinh

FOREIGN PATENT DOCUMENTS

| EP | 2385486 A1 | 11/2011 | |
|---|---|---|---|
| FR | 3044408 A1 * | 6/2017 | ................ G01J 5/34 |
| WO | 2018/020176 A1 | 2/2018 | |

OTHER PUBLICATIONS

Ding et al., "A review of the operating limits in slot die coating processes", AIChE Journal, vol. 62, No. 7, Jul. 2016, pp. 2508-2524.
(Continued)

*Primary Examiner* — Selim U Ahmed
*Assistant Examiner* — Evan G Clinton
(74) *Attorney, Agent, or Firm* — Womble Bond Dickinson (US) LLP

(57) ABSTRACT

The invention relates to a manufacturing process of a pixel array of a thermal pattern sensor comprising the steps of:
  providing a substrate;
  depositing a first layer of electrically conductive material, including depositing electrically conductive tracks, depositing of connector pins and depositing a ground strip;
  depositing of second layer of pyroelectric material covering the tracks and leaving at least part of the connector pins free;
  depositing of third layer of electrically conductive material;
  depositing of fourth layer of dielectric material in contact with the third layer;
  depositing of a fifth layer including electrically conductive heating tracks;
  depositing of a sixth protective layer,
(Continued)

wherein the step of depositing the second and/or third and/or fourth and/or sixth layer is carried out by slot-die coating.

13 Claims, 13 Drawing Sheets

(51) Int. Cl.
    *G01K 7/00*         (2006.01)
    *G06K 9/20*         (2006.01)
    *G06K 9/78*         (2006.01)
    *G01J 5/34*         (2006.01)
    *H01L 37/02*       (2006.01)

(52) U.S. Cl.
    CPC ......... *G01K 7/003* (2013.01); *G06K 9/00026* (2013.01); *G06K 9/00053* (2013.01); *G06K 9/209* (2013.01); *G06K 9/78* (2013.01); *H01L 37/02* (2013.01)

(56) References Cited

OTHER PUBLICATIONS

Preliminary Research Report and Written Opinion received for French Application No. 1857511, dated Jun. 4, 2019, 11 pages (1 page of French Translation Cover Sheet and 10 pages of original document).

\* cited by examiner

MANUFACTURING PROCESS OF A PIXEL ARRAY OF A THERMAL PATTERN SENSOR AND ASSOCIATED SENSOR

GENERAL TECHNICAL FIELD

The invention relates to a manufacturing process of a thermal pattern sensor, for example an "active" fingerprint sensor, performing active or passive heat detection and preferably including an active or passive pixel array. More particularly, the invention relates to the manufacture of the pixel array.

STATE OF THE ART

A fingerprint sensor includes heat detection means. These heat detection means may correspond to pyroelectric elements, diodes, thermistors or any other temperature-sensitive element that converts a temperature change into an electrical potential or current change.

Documents U.S. Pat. No. 6,091,837, EP 2 385 486 A1 and WO 2018/020176 disclose "active" fingerprint sensors that perform active heat detection and include a passive pixel array.

FIG. 1 is a cross-sectional view of the structure of such a sensor, which includes, in particular, the layers below, placed one after the other above a support S0.

Such a support S0 (for example a substrate) is made of PET or PEN or PI, or of a CIU type (ABF, FR4, etc.) material, or of glass.

The first layer 10 consists of a pattern of electrically conductive material (Au, Ag, Al, Cu) with metallic columns M1 and a ground line (not shown).

The second layer 20 is made of a pyroelectric material composed of a copolymer of polyvinylidene fluoride (PVDF) and trifluoroethylene (Trfe) which covers the lines M1.

The third layer 30 is made of electrically conductive material and supports a fourth layer 40 made of dielectric material itself supporting a fifth layer 50 including lines of electrically conductive material, preferably metallic, which will be heated.

Finally, a sixth protective layer 60 covers the whole.

Each pixel is formed by a pyroelectric capacitance itself formed by two electrically and thermally conductive electrodes (but to a lesser extent to avoid a possible lateral thermal short circuit) (first and third layers 10, 30) between which a portion of pyroelectric material is arranged, and a heating element (layer 50). This heating element dissipates a certain amount of heat in the pixel, and the heating of the pixel is measured after a certain acquisition time, called integration time, in the presence of the finger on the sensor. This makes it possible to distinguish, at the level of each pixel, the presence of a ridge or valley of the detected fingerprint depending on whether the heat is absorbed by the skin (pixel in the presence of a ridge of the fingerprint) or stored in the pixel (pixel in the presence of a valley of the fingerprint). This leads to a lower final temperature in the case of a pixel in the presence of a ridge, where heat is absorbed by the skin, in comparison with a pixel in the presence of a valley.

Conventionally, such a sensor can be manufactured using various printing techniques or by subtractive methods such as photolithography, particularly with regard to obtaining the passive pixel array. Not all printing techniques allow access to this device at the same cost. There is also a need to be able to use inexpensive slot-die coating techniques to manufacture such a sensor.

PRESENTATION OF THE INVENTION

One aim of the invention is to propose a pixel array of a thermal pattern sensor, which is a three-dimensional (3D) pattern, obtainable by means of a roll-to-roll or sheet-to-sheet process combined with inexpensive printing/layer deposition techniques.

To that end, the invention proposes, according to a first aspect, a process for manufacturing a pixel array of a thermal pattern sensor, the process comprising the steps of:
providing a substrate;
providing a first layer of electrically conductive material, comprising:
depositing electrically conductive tracks extending in a first direction of elongation;
depositing connector pins, extending from the tracks, in a second direction of elongation, different from the first direction of elongation, and moving towards a first edge of the substrate, called the output edge;
depositing a ground strip to form the ground of the sensor;
forming a second layer of pyroelectric material covering the tracks and leaving at least part of the connector pins free;
forming a third layer of electrically conductive material placed between the layer of pyroelectric material and the ground strip without covering the free part of the connector pins;
forming a fourth layer of dielectric material in contact with the third layer and extending so as to cover the tracks of the first layer;
depositing a fifth layer including electrically conductive heating tracks, said electrically conductive heating tracks extending from the ground strip to the first edge of the substrate so as to cover the tracks of the first layer;
depositing a sixth protective layer;
wherein the step of depositing the second layer and/or the step of depositing the third layer and/or the step of depositing the fourth layer and/or the step of depositing the sixth layer is carried out by slot-die coating.

The invention has several advantages.

The arrangement of the different layers of the pixel array allows simple and inexpensive techniques to be used to manufacture said layers.

Indeed, layers consisting of at least one strip preferentially greater than or equal to 5 mm wide can be deposited by liquid deposition using a technique using a slot die through which the material to be deposited is brought onto the surface in ink form. This technique is known as "slot die" or "slit coating". This technique is highly suitable for the deposition of continuous strips or long strips.

The invention is advantageously complemented by the following features, taken alone or in any of their technically possible combinations:
- the layers are deposited successively as follows: depositing of the first layer, depositing of the second layer, depositing of the third layer, depositing of the fourth layer, depositing of the fifth layer, depositing of the of sixth layer;
- the layers are deposited successively as follows: depositing of the fifth layer, depositing of the fourth layer, depositing of the first layer, depositing of the second layer formation, depositing of the third layer, depositing of the sixth layer;

the first layer further includes a polarization strip connected to columns of the metallic pattern of the first layer;

the tracks of the first layer form a coil, the tracks being connected in pairs by means of metal strips;

the first layer further includes metal blocks intended to be in the extension of the electrically conductive heating tracks of the fifth layer;

the tracks and the connector pins of the first layer form a plurality of Ls nested within each other;

at the end of the process, the connector pins are all below the electrically conductive heating tracks of the fifth layer;

the tracks and the connector pins of the first layer form an alternation of upright and inverted Ls;

the third layer depositing step is carried out in such a way as to provide a space in the second direction of elongation along which the second layer of pyroelectric material remains visible;

during the second layer depositing step, several strips of pyroelectric material are juxtaposed to form several pixel arrays in parallel.

According to a second aspect, the invention relates to a pixel array of a thermal pattern sensor manufactured by a process as defined above.

According to a third aspect, the invention relates to a thermal pattern sensor including a pixel array as defined above, the array being typically passive or active.

PRESENTATION OF THE FIGURES

Other features, aims and advantages of the invention will emerge from the following description, which is purely illustrative and non-limiting, and which must be read in conjunction with the accompanying drawings on which, in addition to FIG. 1 already discussed:

FIG. 2b illustrates a cross-sectional side view of the array in FIG. 2a;

On all the figures the similar elements have the same reference characters.

DETAILED DESCRIPTION OF THE INVENTION

Figure 1:
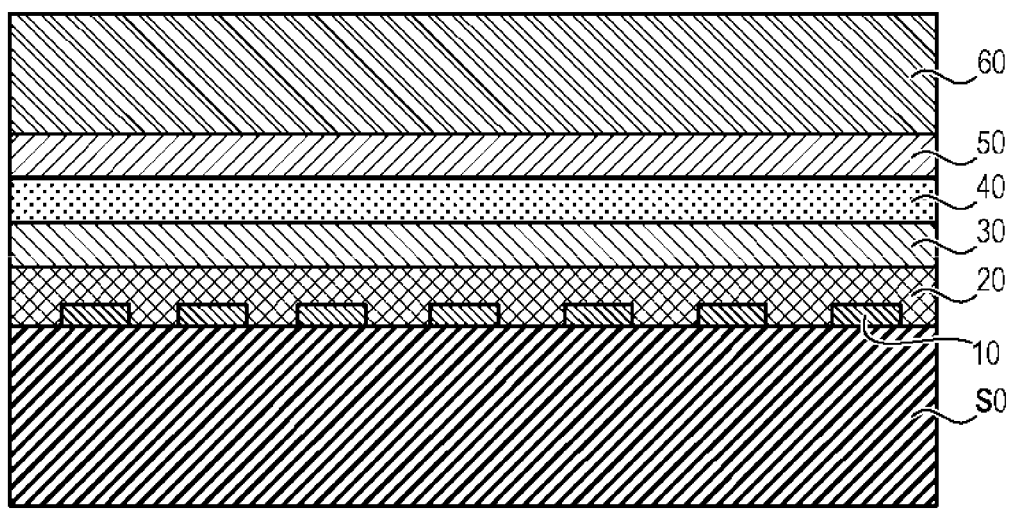
Figure 2A:
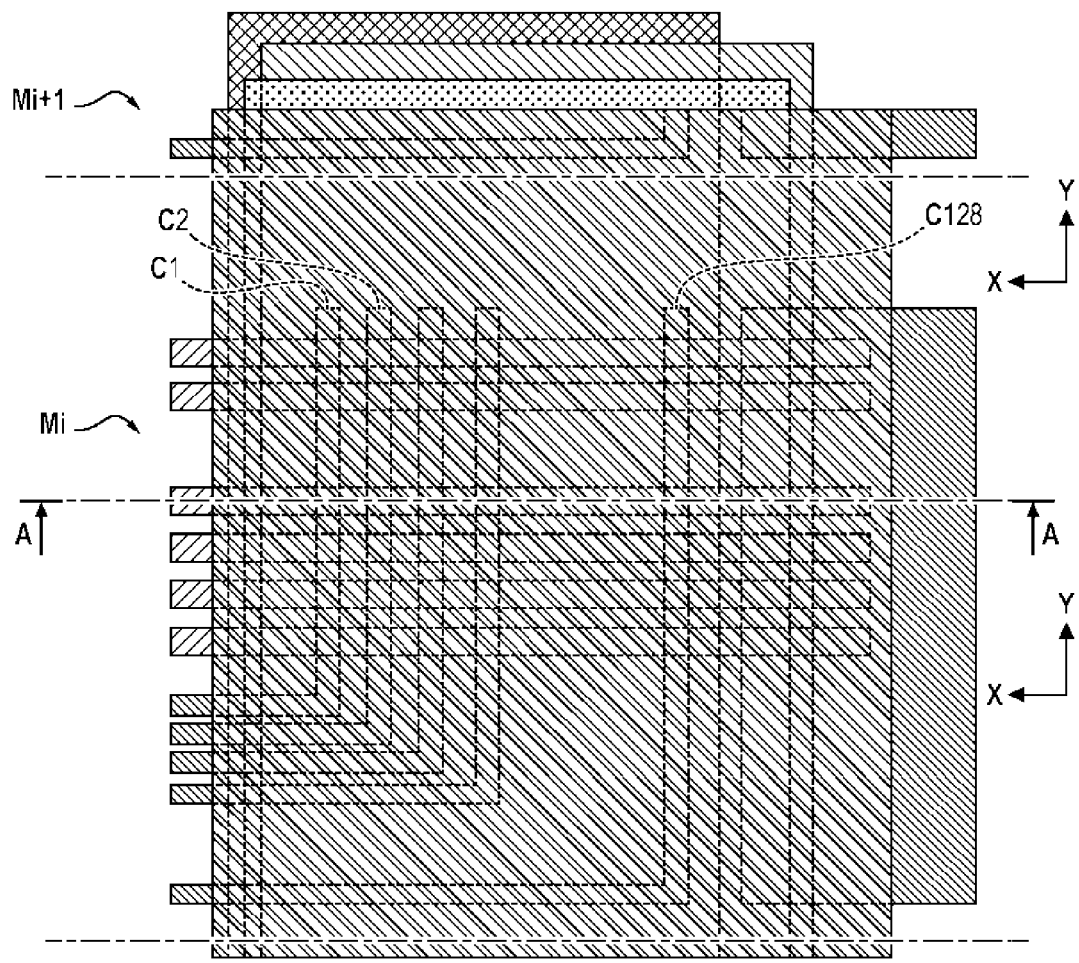
FIG. 2a illustrates a top view of a pixel array according to a first embodiment of the invention.
Figure 2B:
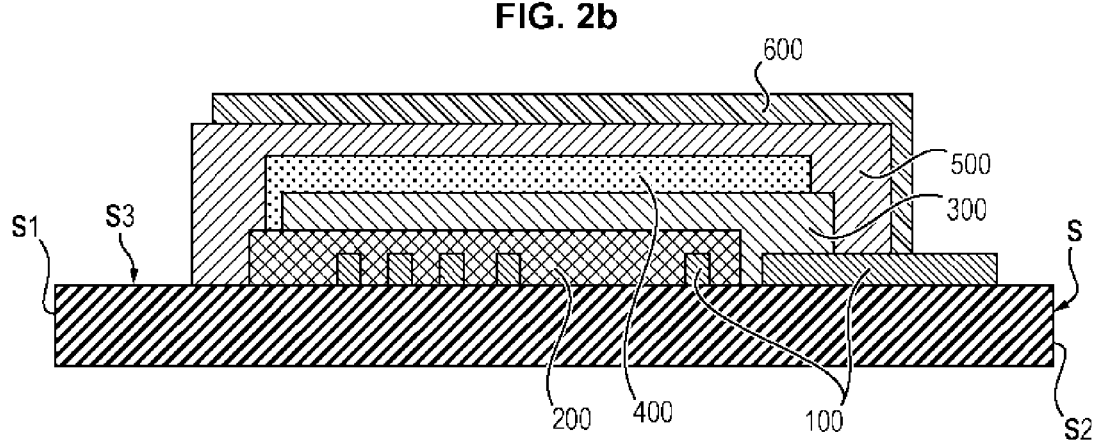

FIG. 2a illustrates a top view of a thermal sensor array according to one embodiment of the invention and FIG. 2b illustrates a side view of a section A-A of the pattern in FIG. 2a.

In this figure, we see a complete pattern Mi and the beginning of the next pattern $M_{i+1}$, the two being separated on the figure by a thick dotted line (it is in fact an imaginary cutting line according to which at the end of all the manufacturing steps the array will be cut along this line).

Indeed, according to a preferred embodiment, and in the following, we consider the case of roll-to-roll printing according to which a roll including a continuous flow of support is unwound to be brought to several printing stages. The advantage of roll-to-roll printing is that it is faster than support-by-support printing and avoids the handling operations to move a support from one printing stage to another.

In addition, roll-to-roll printing makes it possible to handle very thin supports. Indeed, support-by-support handling requires a certain rigidity, whereas on a roll, the tension of the roll makes very thin supports handleable.

It will be understood that several arrays can be obtained over the width of a single roll, the width being measured in a direction substantially perpendicular to an unwinding direction of the roll. The support roll must then be wide enough to juxtapose several strips.

Of course, it is understood that the array can be obtained by means of a printing or slot-die coating process in sheet-to-sheet mode.

In addition, the manufacture of an array is described below.

However, as indicated above, several arrays can be obtained in parallel over the width of the support, subject to the width of the rollers on which the support is wound. In relation to FIGS. 2a and 2b, the array consists of a stack of several layers 100, 200, 300, 400, 500, 600 on a support S such as a substrate.

This stacking is not restrictive as will be seen below.

The support S has a first edge s1, a second edge s2 and a rectangular upper surface s3 having a width along an axis X and a length along an axis Y.

The support S is for example made of glass or of semiconductor material (such as Si). In addition, the support S has a thickness between 25 and 200 microns, typically 50 to 125 microns.

Preferably, and in order to be compatible with a roll-to-roll printing or slot-die coating process, the support S is a flexible material, for example based on polyimide (PI) or polyethylene naphthalate (PEN) or polyethylene terephthalate (PET).

Several layers are deposited on this support S, typically by slot-die coating techniques which will be described below.

Figure 3A:
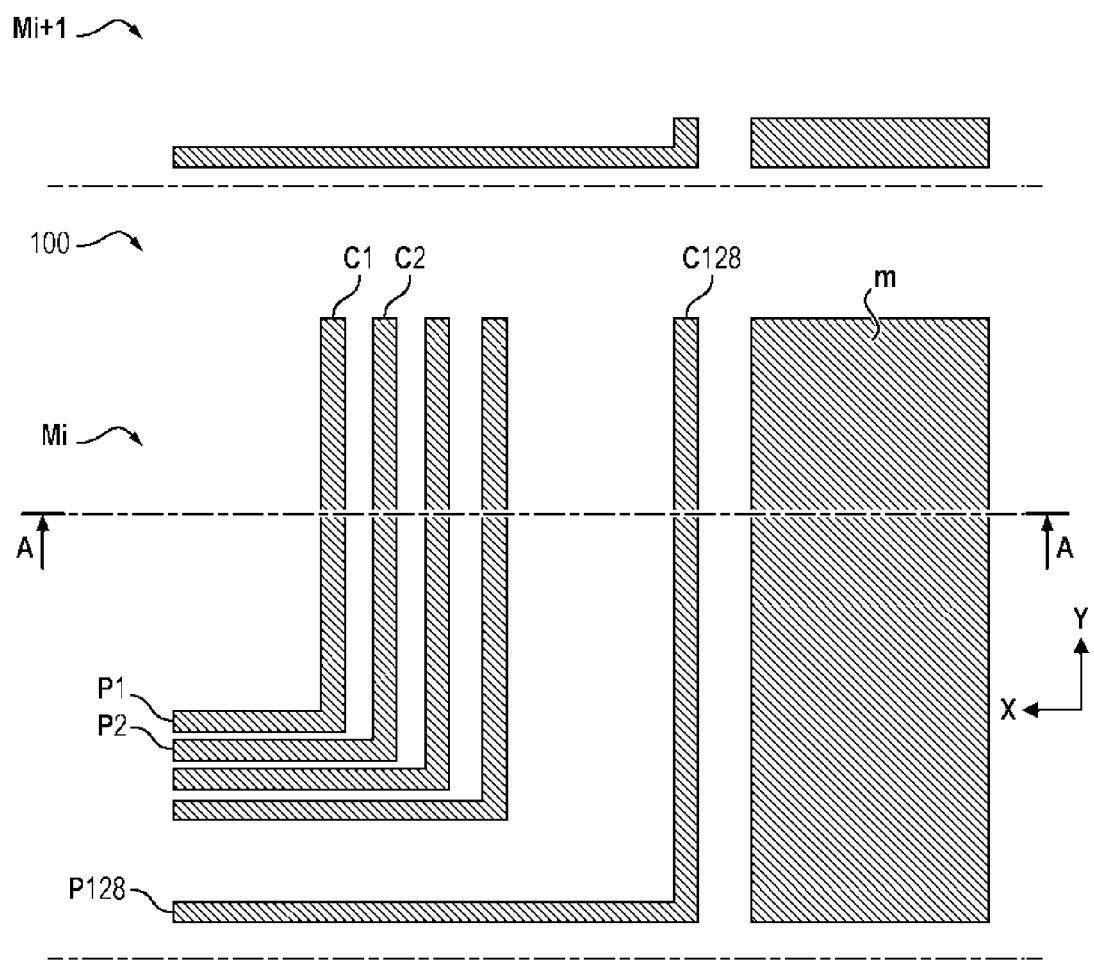
FIGS. 3a to 8b illustrate the deposition of successive layers during a manufacturing process for a pixel array according to the invention.
Figure 3B:
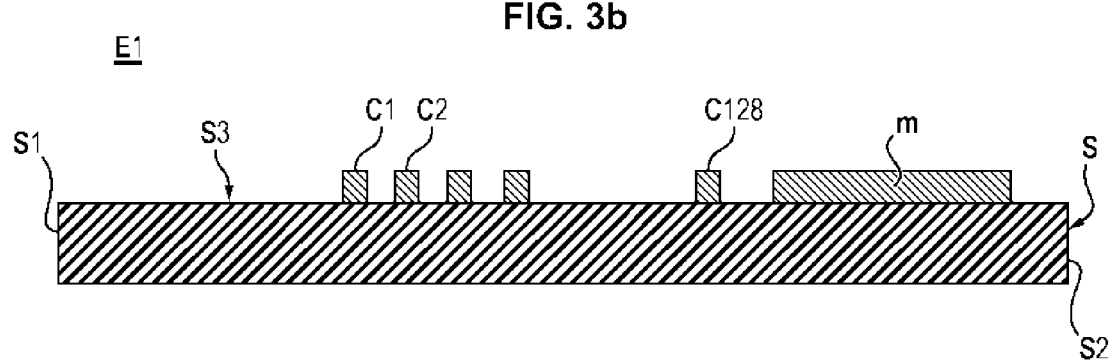

A first layer 100 includes an electrically conductive pattern (see FIGS. 3a and 3b), the electrically conductive metal pattern including Tracks forming columns $c_1, c_2, c_{128}$ of the pixel array and forming the lower electrode. These tracks are parallel to each other in a first direction of elongation (along the axis Y). Typically, the array includes 128 tracks.

Connector pins $p_1, p_2, p_{128}$, extending from the tracks, in a second direction of elongation (along the axis X), and moving towards a first edge of the support S called the output edge (i.e. the edge by which the connections/soldering will be made).

a ground strip m parallel to the tracks and extending along a second edge opposite the first edge (along the axis Y);

The electrically conductive pattern is made of metallic material, typically gold, or a less precious metal (silver, aluminum or copper, etc.). The thickness of the metallic pattern is between 50 and 200 nm.

Note that FIG. 2b is a section along the axis AA so that the connector pins are not visible.

This first layer is advantageously deposited by offset printing, engraving or gravure printing, lithography or laser structuring. It should be noted that strips of constant width are deposited.

The offset technique consists in that a cylinder deposits the metal on a second cylinder which passes over the support S. Of course, the diameter of the roller must be correctly arranged to make regular patterns. This printing technique has the advantage of printing precise patterns.

A second layer 200 (see FIGS. 4a and 4b), including, preferably a rectangular strip 221, of pyroelectric material covering the tracks $c_1$, $c_2$, $c_{128}$ and leaving at least part of the connector pins $p_1$, $p_2$, $p_{128}$ free.

A pyroelectric material is for example P(VDF-TrFE) or PVDF. Other variants can be considered for the choice of material as long as it is adapted to form a pyroelectric capacity.

Figure 4A:
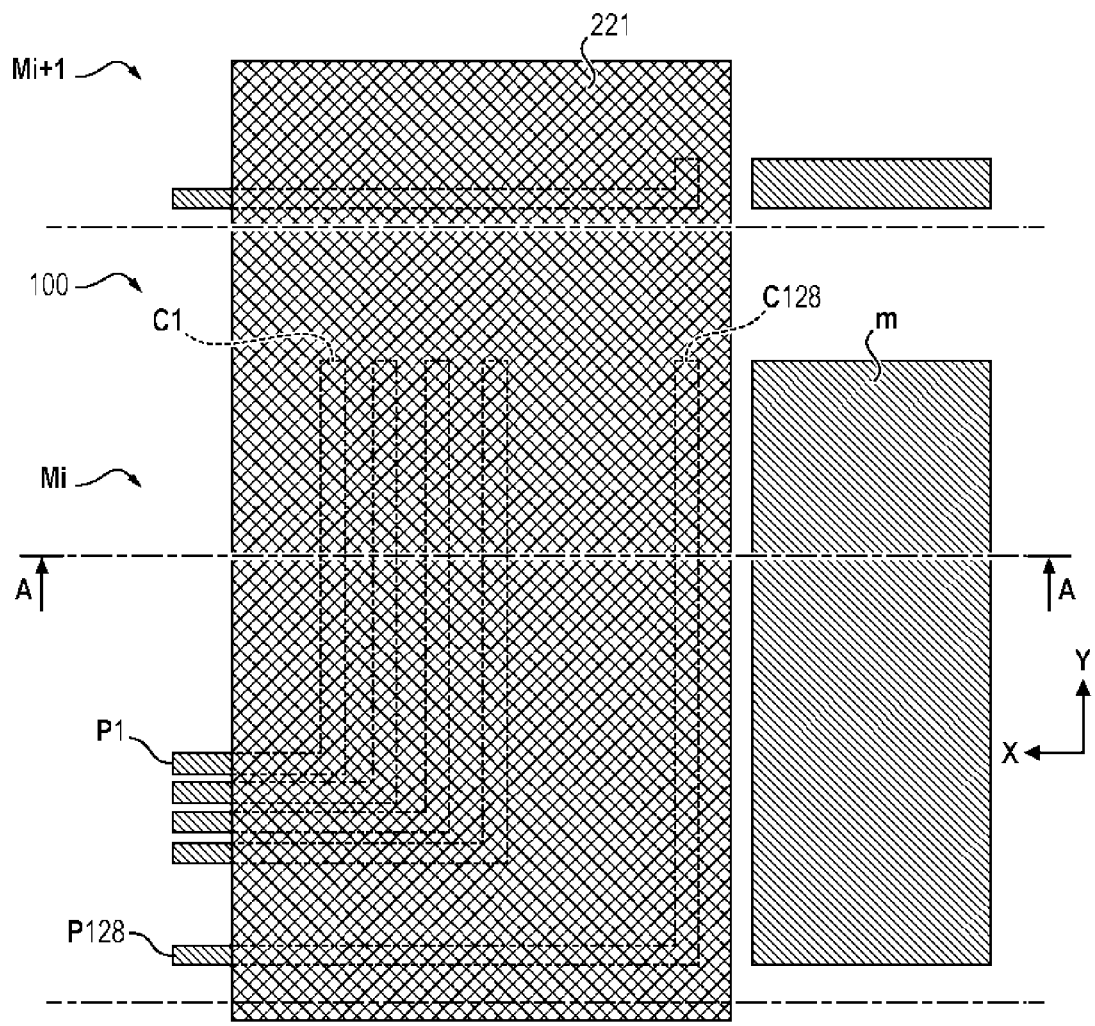
Figure 4B:
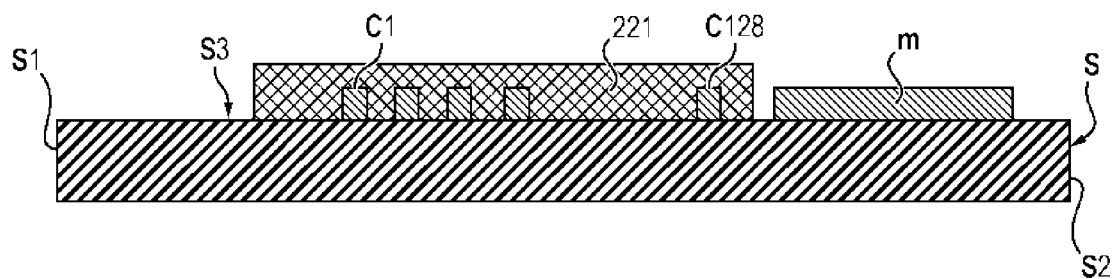

As shown in FIG. 4a, the strip 221 is of constant width (rectangular in FIG. 4a) and covers the tracks $c_1$, $c_2$, $c_{128}$ but not all the connector pins $p_1$, $p_2$, $p_{128}$ which are left visible for connections/soldering. Similarly, the strip 221 of pyroelectric material does not cover (even partially) the ground strip m. Thus, there may be a gap between the strip 221 of pyroelectric material and the rectangular ground strip m.

By way of example, the thickness of the second layer 200 (pyroelectric material) is between 1 and 10 microns, preferably from 2 to 5 microns and more preferentially 3 microns.

This second layer 200 is advantageously deposited by means of slot-die coating making a continuous strip in the unwinding direction of the roll or making long strips in the case of a sheet-to-sheet mode or making a juxtaposition of several strips when several arrays are manufactured in parallel. Preferably, during the deposition step the strips extend between each cutting line, the rectangular shape being obtained after cutting the array.

Optionally, the layer of pyroelectric material can be deposited in two (or more) passes, or two successive layers to facilitate and obtain a more homogeneous deposition, especially when the final thickness becomes large, for example 5 microns.

A third layer 300 (see FIGS. 5a and 5b) including a strip 331 of constant width of electrically conductive material straddling between the strip 221 of pyroelectric material of the second layer and the ground strip m without completely covering the free portion of the connector pins of the first layer. This third layer is advantageously deposited by means of slot-die coating making a continuous strip in the unwinding direction of the roll or by making long strips in the case of a sheet-to-sheet mode or a juxtaposition of several strips when several arrays are manufactured in parallel. Preferably, during the depositing step the strips extend between each cutting line, the rectangular shape being obtained after cutting the array. This third layer 300 constitutes an upper electrode for the sensor array and is typically made of PEDOT:PSS or silver-based conductive ink.

Figure 5A:
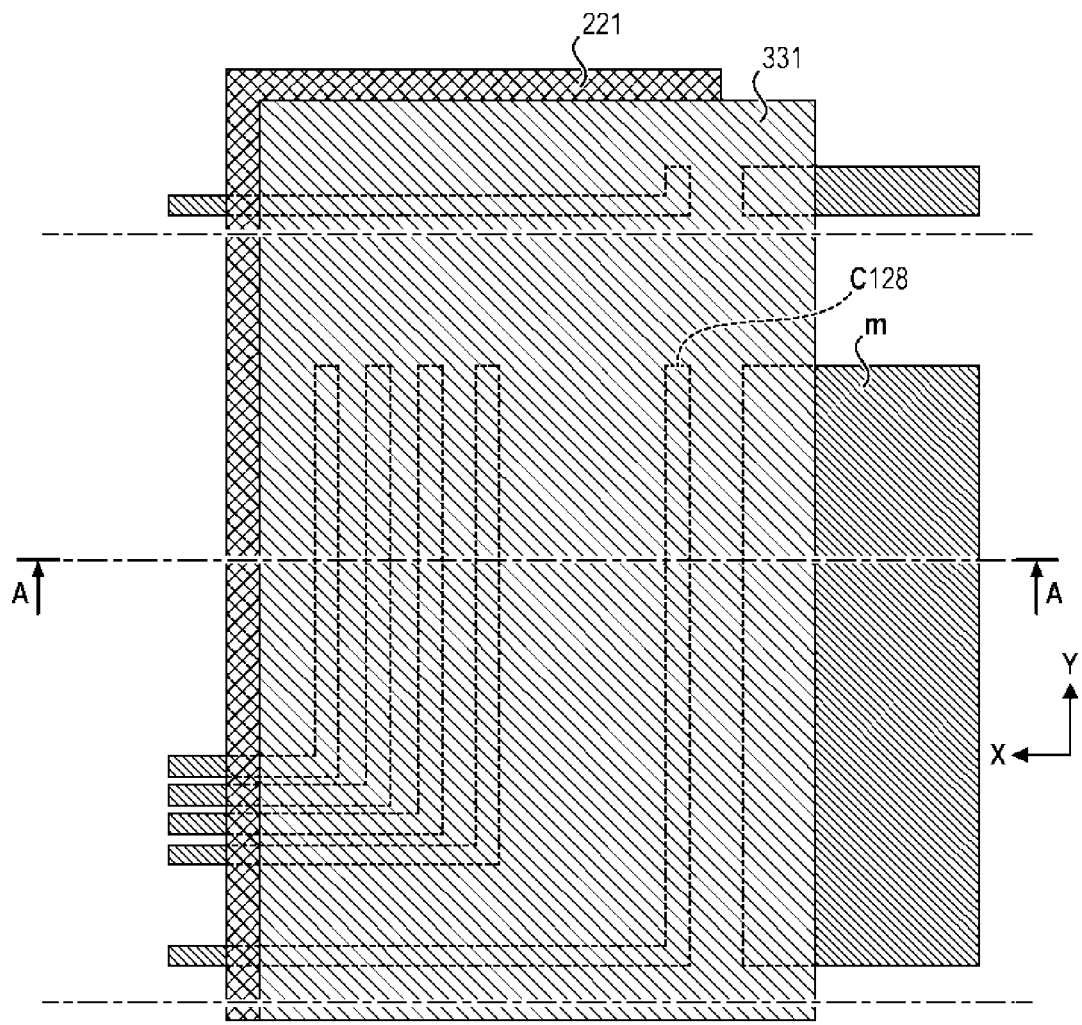
Figure 5B:
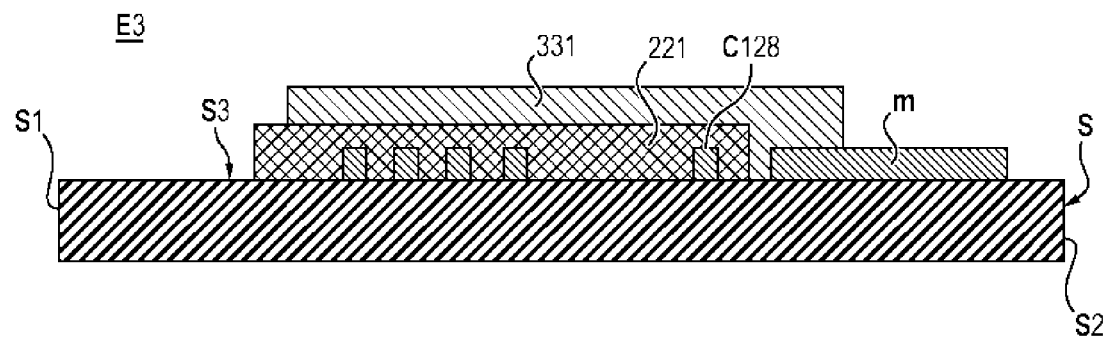

As shown in FIG. 5a, the strip 331 of the third layer 300 is connected to the ground strip m. Here again, the connector pins $p_1$, $p_2$, $p_{128}$ are left visible.

Preferably, a part of the rectangular strip 221 of pyroelectric material is left visible along the first edge S1 of the support S after the depositing of the strip 331 of electrically conductive material. A space is provided in the second direction of elongation X along which the strip 221 of pyroelectric material remains visible.

By way of example, the thickness of the third layer is between 100 and 2000 nanometers, preferably less than 1000 nanometers and more precisely around 400 nm.

Figure 6A:
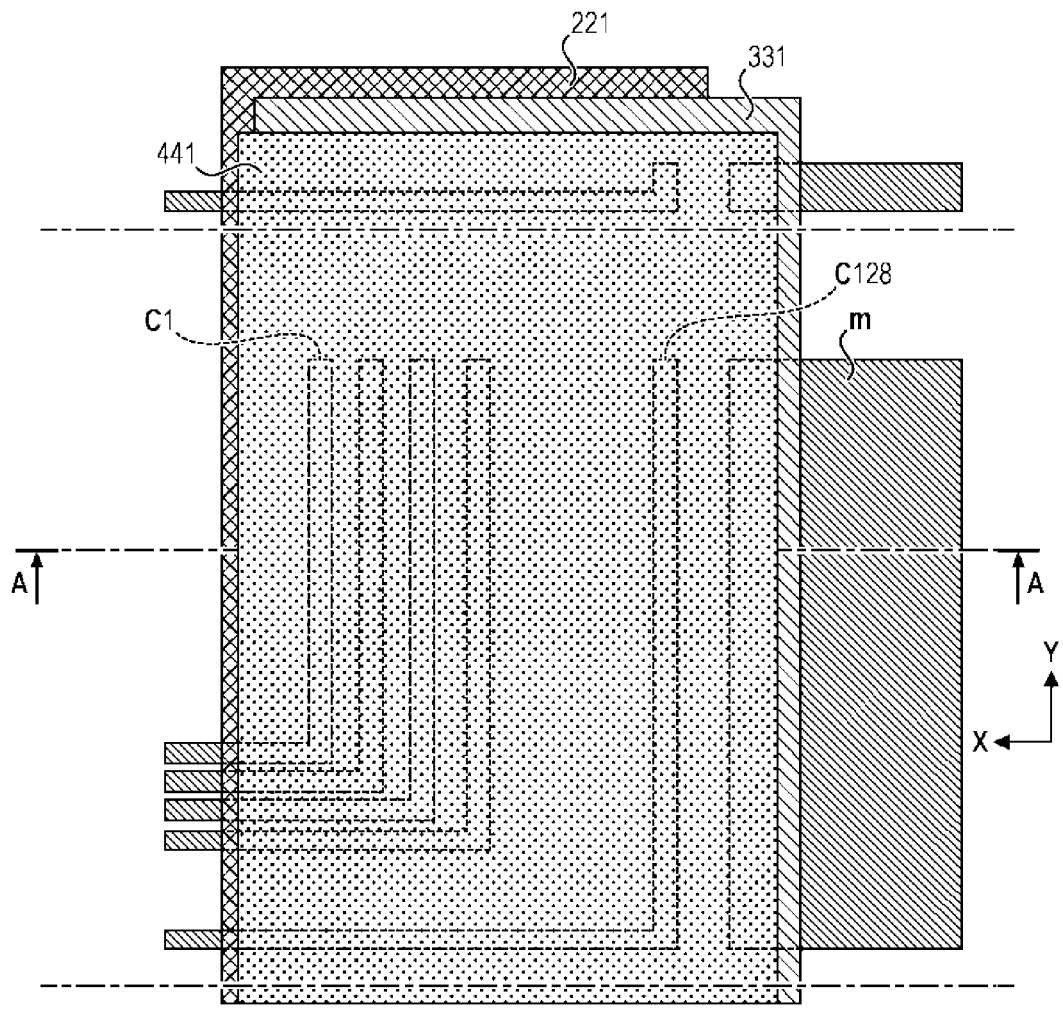
Figure 6B:
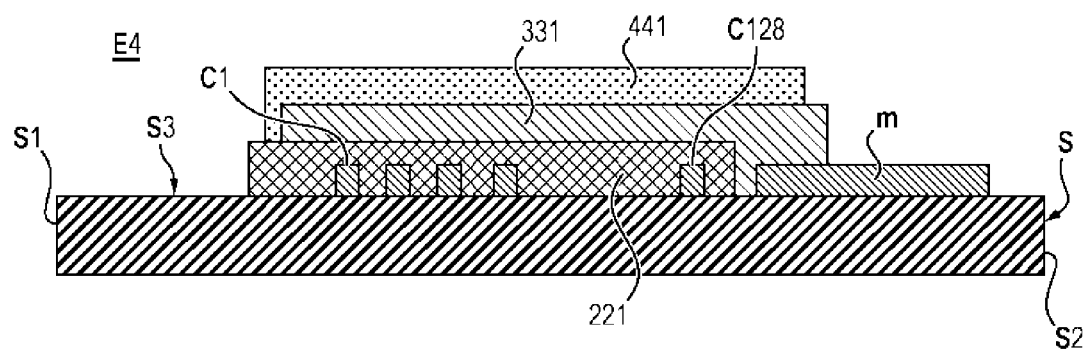

A fourth layer 400 (see FIGS. 6a and 6b) including a strip 441 of constant width made of dielectric material in contact with the strip 221 of pyroelectric material of the second layer 200 and the strip 331 of metallic material of the third layer 300.

The rectangular strip 441 of dielectric material is in contact with the third layer 300 and extends so as to cover the tracks of the first layer 100.

This fourth layer 400 is advantageously deposited by slot-die coating by making a continuous strip in the unwinding direction of the roll or by making long strips in the case of a sheet-to-sheet mode or by juxtaposing several strips when several arrays are manufactured in parallel. Preferably, during the depositing step the strips extend between each cutting line, the rectangular shape being obtained after cutting the array.

Figure 7A:
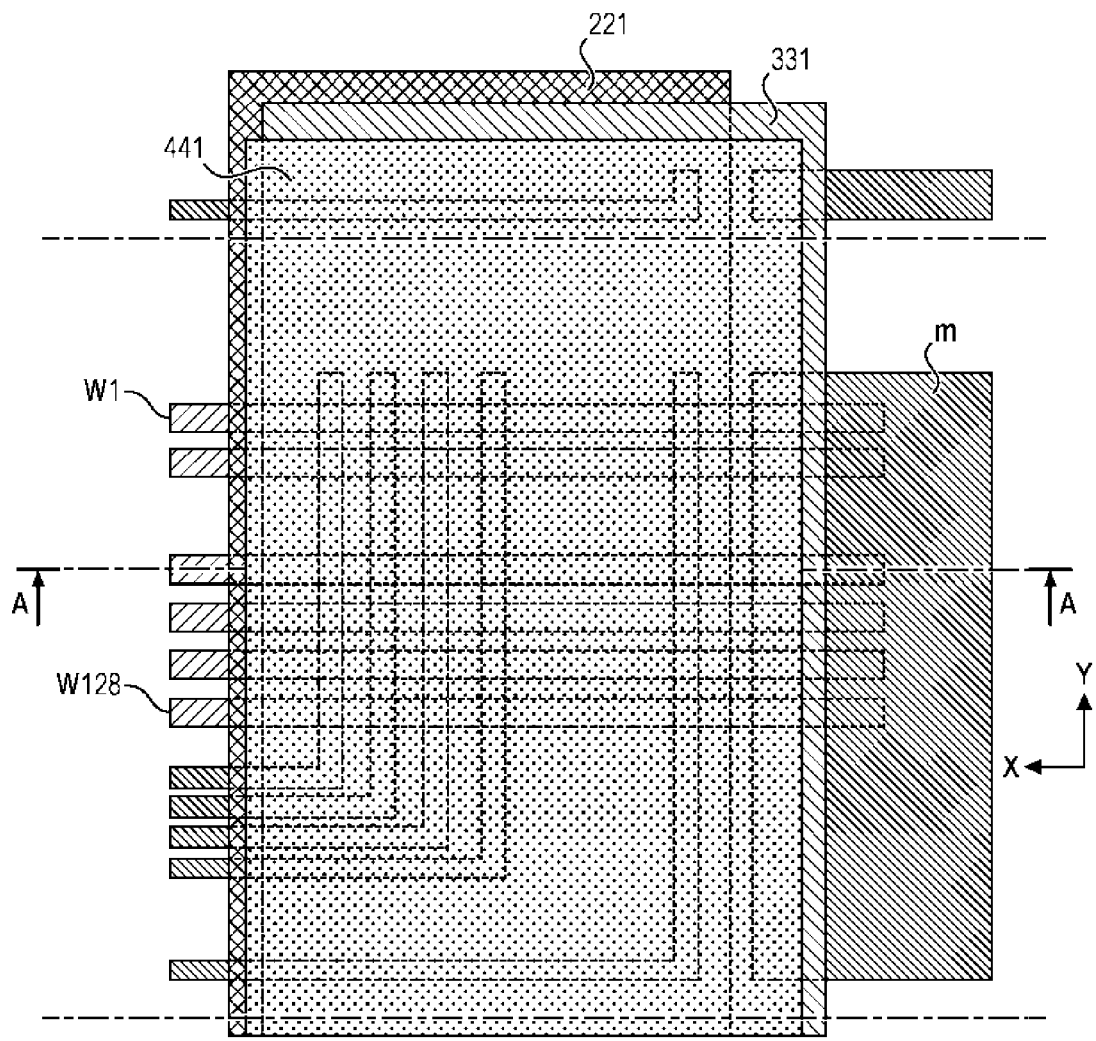
Figure 7B:
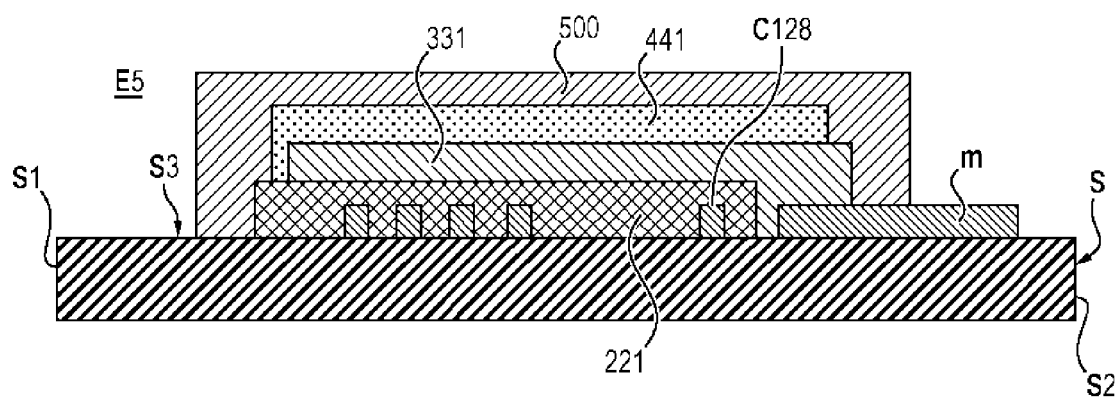

A fifth layer 500 (see FIGS. 7a and 7b) including electrically conductive heating tracks $w_1$, $w_2$, $w_{128}$ arranged extending from the ground strip of the first layer to the first edge of the support S so as to cover the tracks of the first layer.

These tracks are the lines of the pixel array.

The heating tracks $w_1$, $w_2$, $w_{128}$ are connected to the ground strip and do not go beyond the connector pins $p_1$, $p_2$, $p_{128}$. In addition, the electrically conductive heating tracks $w_1$, $w_2$, $w_{128}$ are connected to the upper electrode formed by the third layer 300 or to the ground strip m. It should be noted that in the case where the fourth layer 400 extends beyond the strip 331 of the third layer 300, the electrical contact is always ensured since the two layers are connected to the same ground strip.

By way of example, the electrically conductive heating tracks are made of metallic material, typically gold, or a less-expensive metal (silver, aluminum or copper, etc.). The thickness of the metal heating strips is between 20 and 2000 nm, typically 500 to 1000 nm. The choice of metal is not very important, the essential thing is to have a controlled resistance.

This fifth layer 500 is advantageously deposited by means of offset or gravure printing or physical vapor deposition (PVD) combined with a photolithography or laser structuring means.

Figure 8A:
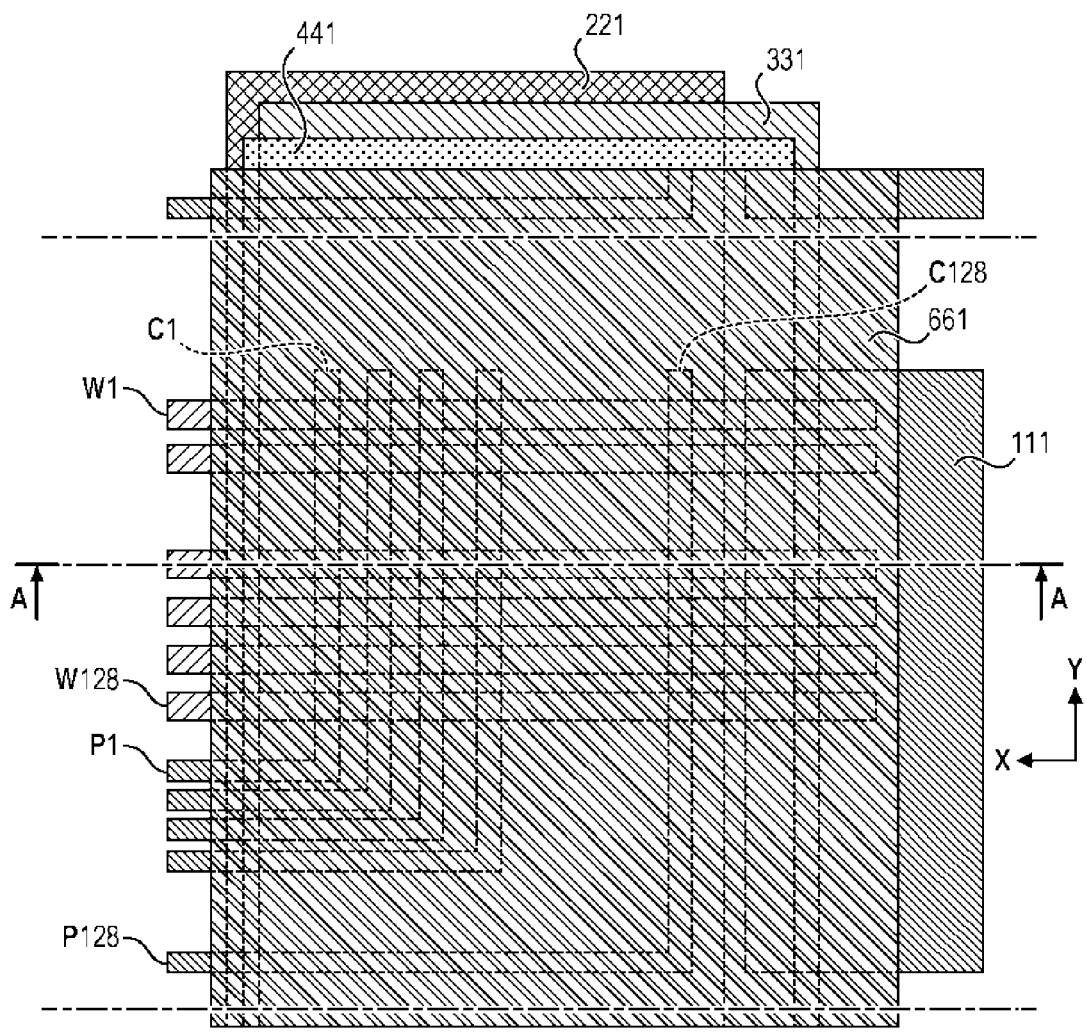
Figure 8B:
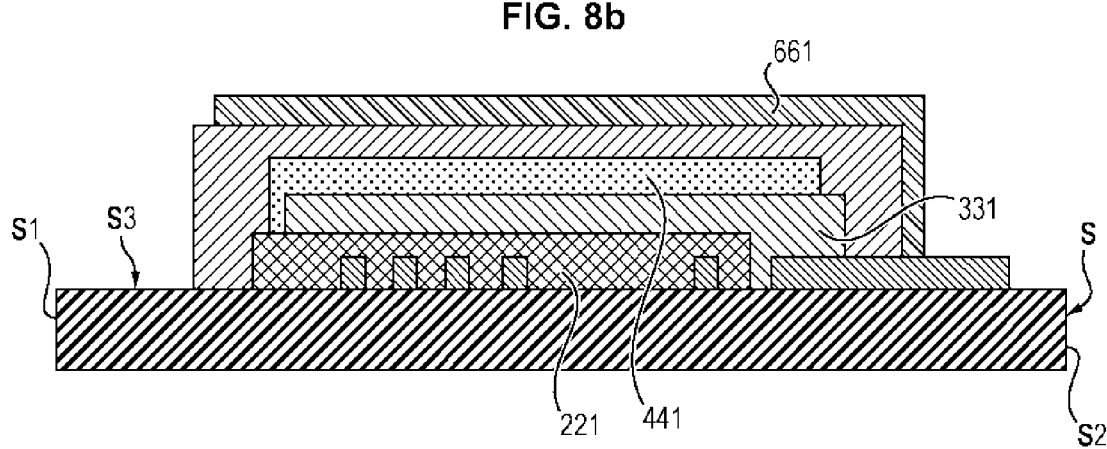

A sixth layer 600 (see FIGS. 8a and 8b) including a protective strip 661 of constant width extending along the axis X from the ground strip m to the first edge s1 of the support S.

The rectangular protective strip 661 is such that it leaves the connector pins and the ends of the heating tracks w visible.

The thickness of the rectangular protective strip must be optimized to protect the layers below while allowing heat to pass through.

For example, the thickness of the sixth layer is between 2 and 10 microns.

This sixth layer 600 is advantageously deposited by means of slot-die coating by making a continuous strip in the unwinding direction of the roll or by making long strips in the case of a sheet-to-sheet mode or by juxtaposing several strips when several arrays are manufactured in parallel. Preferably, during the depositing step the strips extend between each cutting line, the rectangular shape being obtained after cutting the pattern.

In addition, this sixth layer 600 is advantageously made of material: DYMAX OC3021, DYMAX OC4122, PHC XH100, UVHC7300, UVL3.

Figure 9:
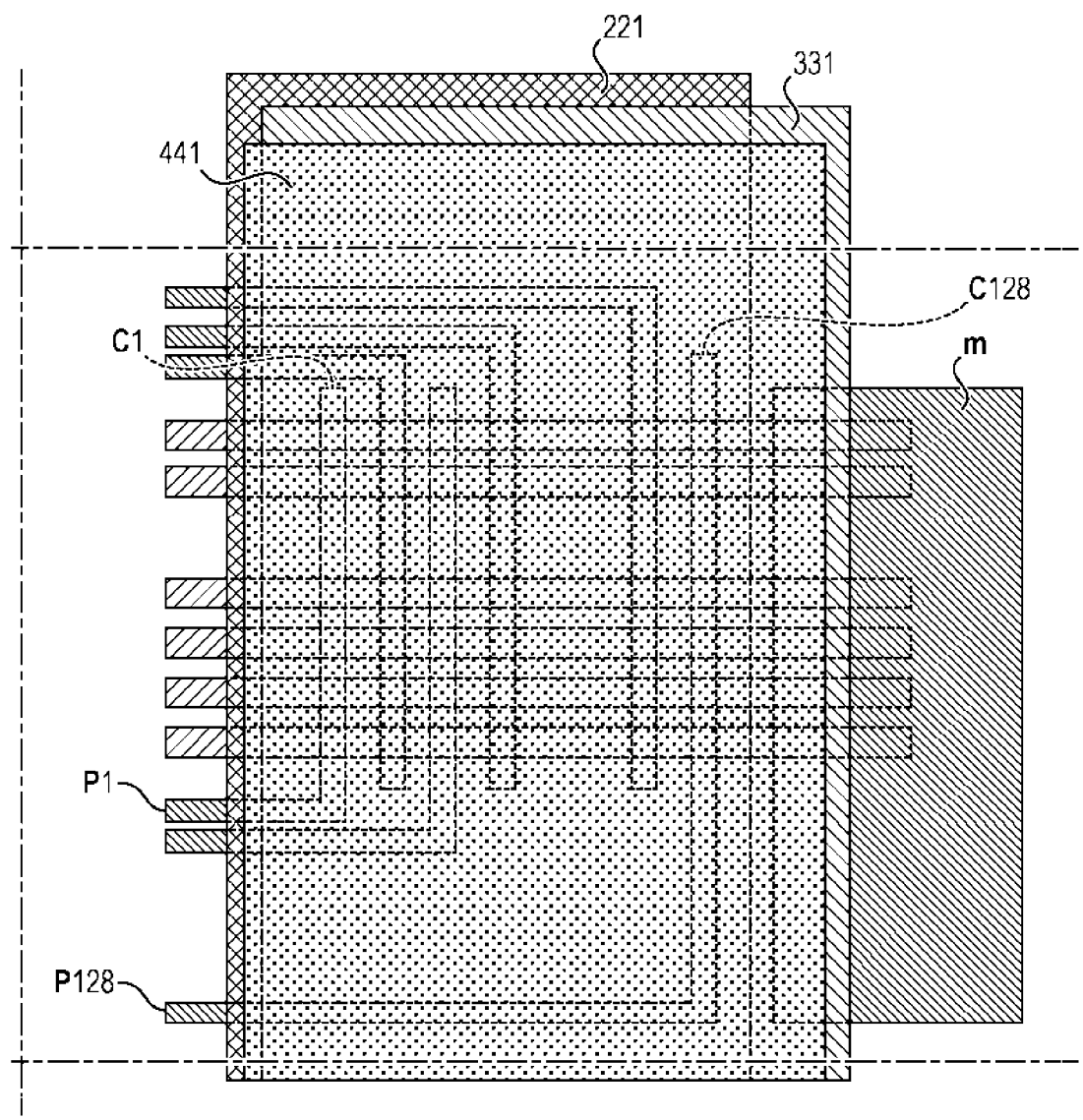
FIG. 9 illustrates a top view of a pixel array according to a second embodiment.

FIG. 9 illustrates an array according to a second embodiment.

This second embodiment differs from the first embodiment by the arrangement of the connector pins $p_1$, $p_{128}$ of the first layer 100.

In particular, the tracks and the connector pins of the first layer form an alternation of upright and inverted Ls so that the connector pins are partly above the electrically conductive heating tracks of the fifth layer and partly below the electrically conductive heating tracks in a direction Y of the support S.

Figure 10:
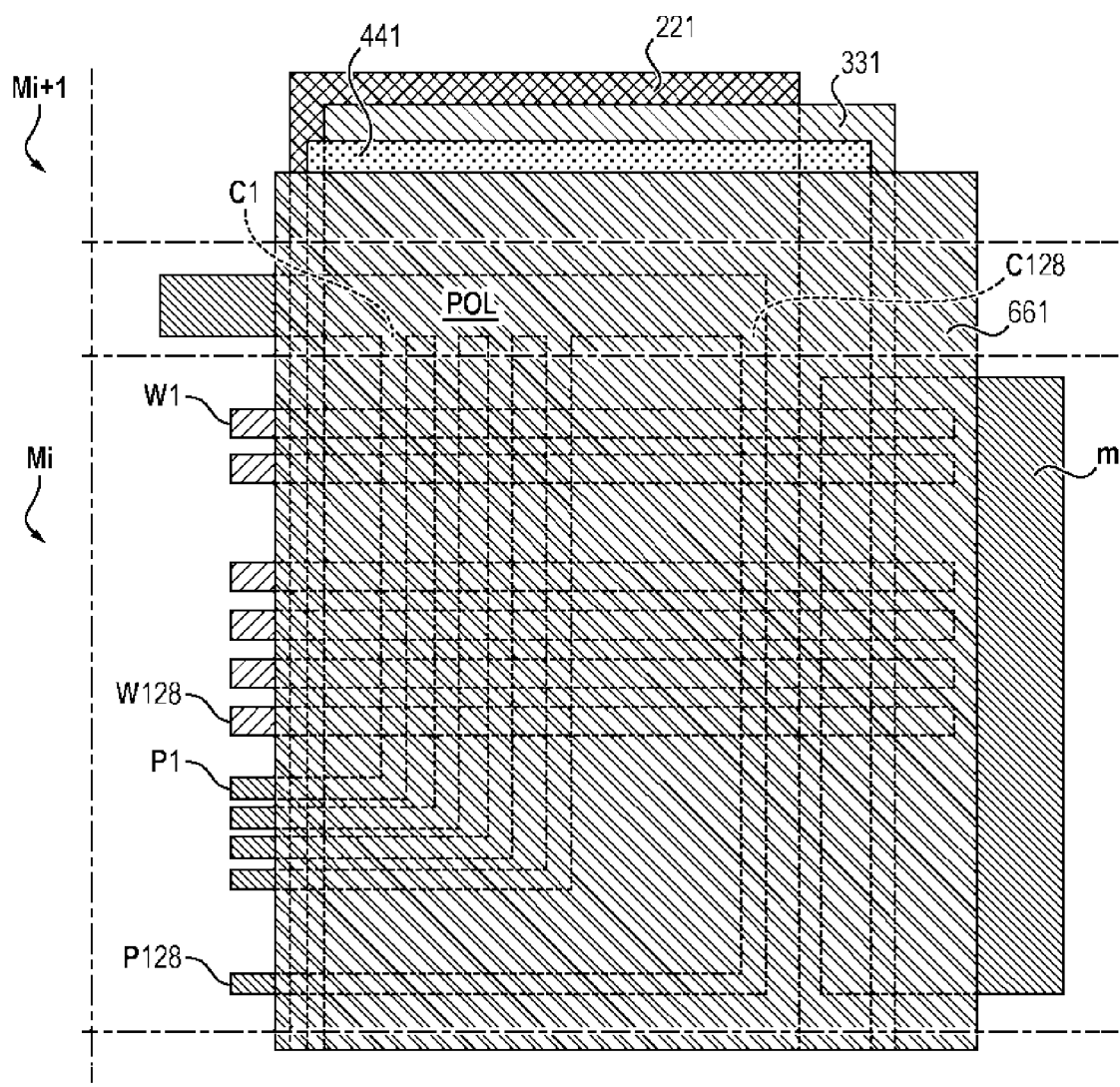
FIG. 10 illustrates a top view of a pixel array according to an embodiment complementary to the first embodiment.

In relation to FIG. 10 and in addition to the first embodiment, it can be expected that the first layer further includes a polarization strip POL connected to the tracks $c_1$, $c_{128}$. This polarization strip POL is in this case printed between two-pixel arrays $M_i$, $M_{i+1}$.

Indeed, for the pyroelectric material to acquire its pyroelectric properties, it must be polarized once and for all by subjecting it to an electric field of about 100 to 120 volts per micron of thickness of the pyroelectric material, for example 350 volts per 3 microns. It is through the tracks of the first layer that the pyroelectric material of the second layer 120 directly above the columns of the first layer 110 will be polarized.

In addition, this embodiment of FIG. 10 provides for tracks of the first layer that are larger than those provided for in the first embodiment, in order to allow all the tracks to be connected.

Once the pyroelectric material is polarized, the area with the polarization strip is cut.

Figure 11:
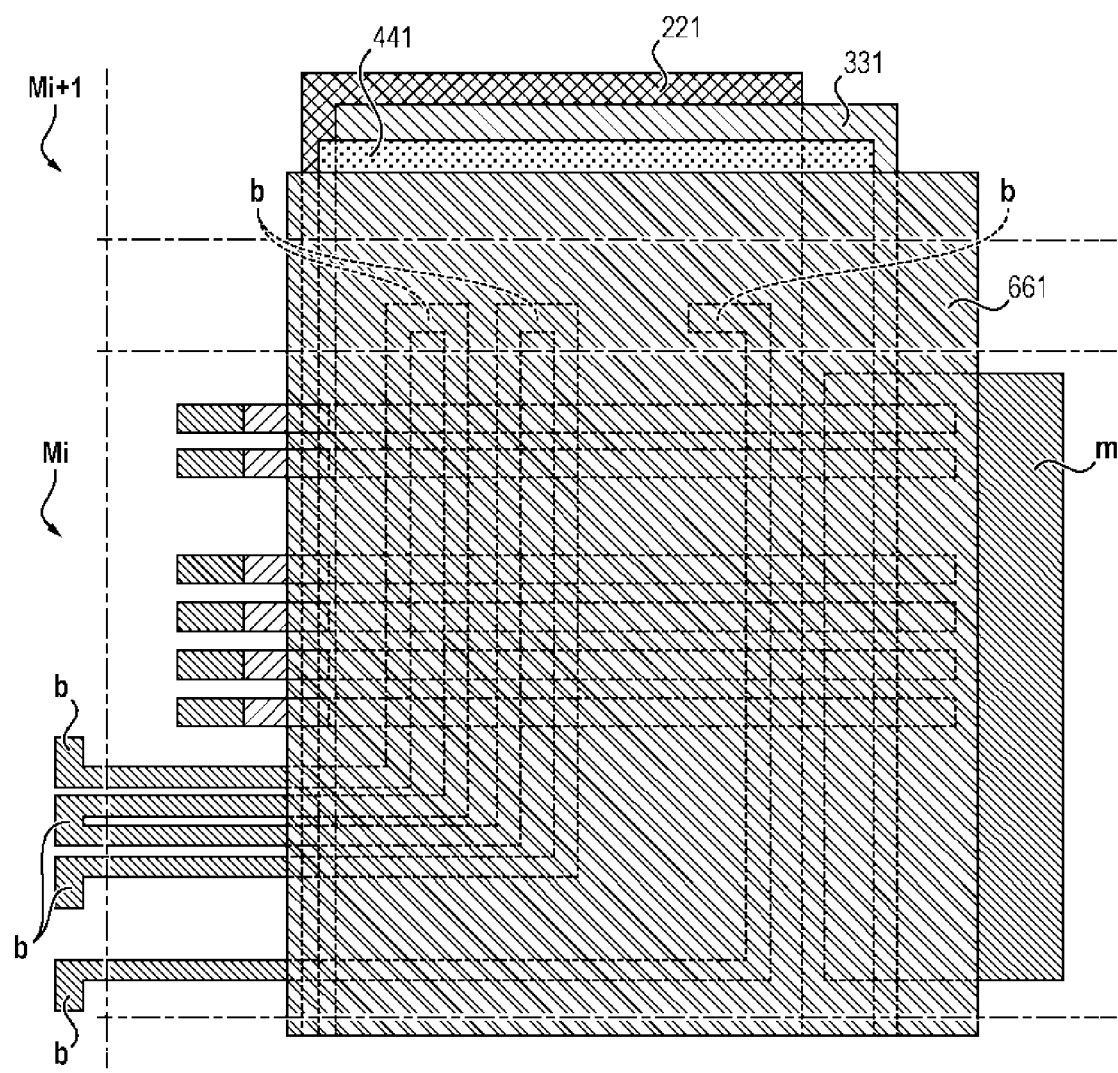
FIG. 11 illustrates a top view of a pixel array according to an embodiment complementary to the first embodiment.
Figure 12:
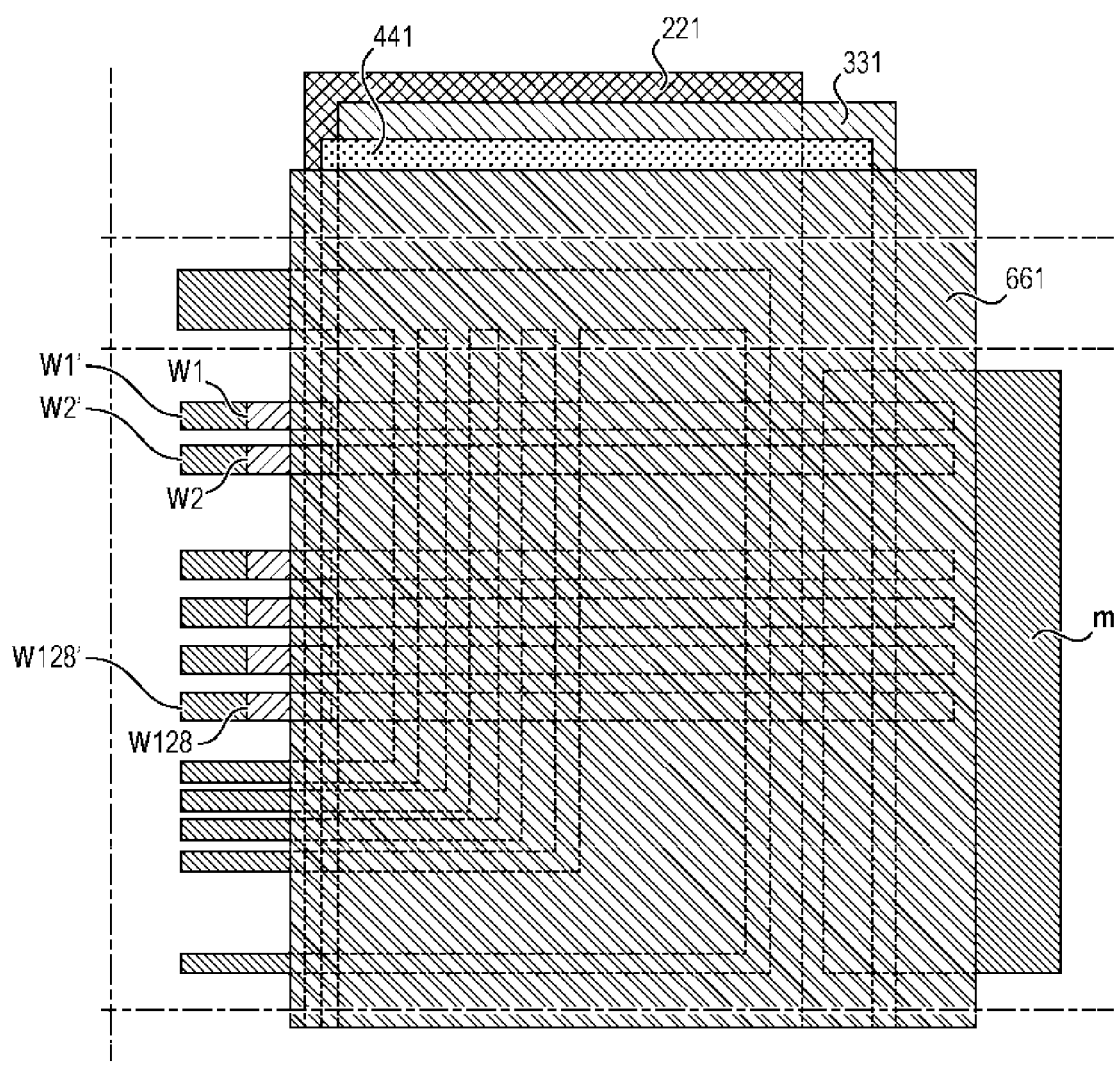
FIG. 12 illustrates a top view of a pixel array according to an embodiment complementary to the first embodiment or to the second embodiment.

Also for polarization purposes, in relation to FIG. 11, as a variant, the tracks $c_1$, $c_2$ of the first layer are expected to form a coil, the tracks being connected by means of metallic strips b in areas that are intended to be cut, one area being located between two pixel arrays $M_i$, $M_{i+1}$ and the other area, beyond the output edge (see the vertical cutting line on the left in FIG. 12). It should be noted that it is in this area that the polarization strip is printed.

Thanks to this arrangement in FIG. 11, it is then possible to control all the tracks with only one resistance measurement and only two points (instead of 128+1 in FIG. 10 (and impossible in the first embodiment since the other side does not exit).

In relation to FIG. 12, in addition to the first embodiment or to the second embodiment, the electrically conductive heating tracks are expected to end at the output edge with electrically conductive blocks $w_{1'}$, $w_{2'}$, $w_{128'}$. The electrically conductive blocks are made of the same material as that used for the first layer and are made at the same time as the latter. Thus, the rows and columns of the array exit through the output edge in a single metal, which facilitates subsequent connections. In addition, the fourth layer 400 can be completely covered by the fifth layer 500 to protect it. This is particularly favorable in the case of a silver layer to prevent its sulfidation.

Figure 13:
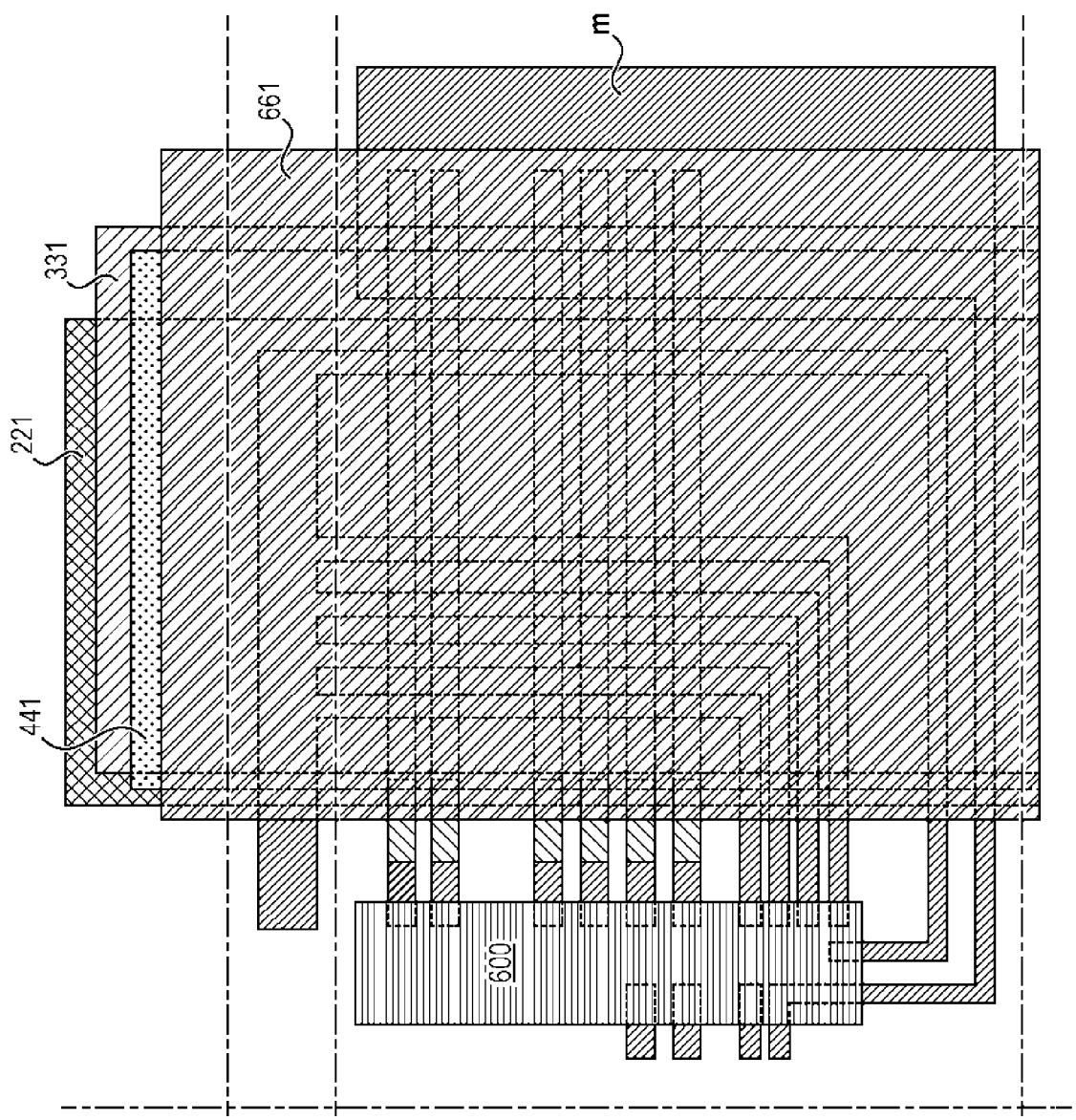
FIG. 13 illustrates a top view of a pixel array according to an embodiment complementary to the embodiment of FIG. 12.

Such blocks are very advantageous when it comes to connecting the rows and columns of the array to a silicon chip 700 as shown in FIG. 13. The chip 700 is flip-chip mounted, i.e., head down with its contact pads down in front of the metal areas exiting through the output edge.

Advantageously, the manufacturing process of the array comprises the following steps implemented successively:

depositing E1 the first layer including the deposition of the tracks, the deposition of the connector pins and the deposition of the ground strip;
depositing E2 the second layer;
depositing E3 the third layer;
depositing E4 the fourth layer;
depositing E5 the fifth layer;
depositing E6 the sixth layer.

According to a second manufacturing, the manufacturing process of the array comprises the following steps implemented successively:

depositing E5 the fifth layer;
depositing E4 the fourth layer;
depositing E1 the first layer including depositing the tracks, the depositing of the connector pins and the depositing of the ground strip;
depositing E2 the second layer;
depositing E3 the third layer;
depositing E6 the sixth layer.

The array thus described therefore has the advantage of being obtained by means of a roll-to-roll printing technique including several stages of slot-die coating.

In addition, by providing the connector pins on one side of the support S, pixel arrays can be printed in continuous flow on a support S that runs from stage to stage.

The invention claimed is:

1. Manufacturing process of a pixel array of a thermal pattern sensor, the process comprising the following steps:
   providing of a substrate (S);
   forming (E1) of a first layer (100) of electrically conductive material, including:
      depositing electrically conductive tracks extending in a first direction of elongation;
      depositing connector pins, extending from the tracks, in a second direction of elongation, different from the first direction of elongation, and moving towards a first edge of the substrate (S), called the output edge;
      depositing a ground strip intended to form the ground of the sensor;
   depositing (E2) a second layer (200) of pyroelectric material covering the tracks and leaving at least part of the connector pins free;
   depositing (E3) a third layer (300) of electrically conductive material placed between the layer of pyroelectric material and the ground strip without covering the free part of the connector pins;
   depositing (E4) a fourth layer (400) of dielectric material and extending in front of the tracks of the first layer;
   depositing (E5) a fifth layer (500) including electrically conductive heating tracks, said electrically conductive heating tracks extending from the ground strip to the first edge of the substrate (S) so as to be above the tracks of the first layer;
   depositing (E6) a sixth protective layer (600);
   wherein the step of depositing the second layer (200) and/or the step of depositing the third layer and/or the step of depositing the fourth layer and/or the step of depositing the sixth layer is carried out by slot-die coating.

2. Manufacturing process according to claim 1, wherein the layers are deposited successively as follows: depositing of the first layer, depositing of the second layer, depositing of the third layer, depositing of the fourth layer, depositing of the fifth layer, depositing of the sixth layer, depositing of the fourth layer, the fourth layer being in contact with the third layer.

3. Manufacturing process according to claim 1, wherein the layers are deposited successively as follows: depositing of the fifth layer, depositing of the fourth layer, depositing of the first layer, depositing of the second layer, depositing of the third layer, depositing of the sixth layer.

4. Manufacturing process according claim 1, wherein the first layer (100) further includes a polarization strip connected to columns of the metallic pattern of the first layer.

5. Manufacturing process according to claim 1, wherein the tracks of the first layer form a coil, the tracks being connected in pairs by means of metal strips.

6. Manufacturing process according to claim 1, wherein the first layer further includes metal blocks intended to be in the extension of the electrically conductive heating tracks of the fifth layer.

7. Manufacturing process according to claim 1, wherein the tracks and the connector pins of the first layer form a plurality of Ls nested within each other.

8. Manufacturing process according to claim 1, at the end of which the connector pins are all below the electrically conductive heating tracks of the fifth layer.

9. Manufacturing process according claim 1, wherein the tracks and the connector pins of the first layer form an alternation of upright and inverted Ls.

10. Manufacturing process according to claim 1, wherein the step of depositing (E3) the third layer (300) is carried out so as to provide a space in the second direction of elongation along which the second layer (200) of pyroelectric material remains visible.

11. Manufacturing process according to claim 1, wherein during the step of depositing (E2) the second layer (200), a juxtaposition of several strips of pyroelectric material is carried out in order to produce several pixel arrays in parallel.

12. Pixel array of a thermal pattern sensor manufactured by a process according to claim 1.

13. Thermal pattern sensor including a pixel array according to claim 12, the array being typically passive or active.

\* \* \* \* \*